US009014835B2

(12) United States Patent
Azernikov et al.

(10) Patent No.: US 9,014,835 B2
(45) Date of Patent: Apr. 21, 2015

(54) SEMI-AUTOMATIC CUSTOMIZATION OF PLATES FOR INTERNAL FRACTURE FIXATION

(75) Inventors: Sergei Azernikov, Acton, MA (US); Suraj Ravi Musuvathy, Lawrence, NJ (US); Tong Fang, Marlboro, NJ (US)

(73) Assignee: Siemens Aktiengesellschaft, Munich (DE)

( * ) Notice: Subject to any disclaimer, the term of this patent is extended or adjusted under 35 U.S.C. 154(b) by 210 days.

(21) Appl. No.: 13/817,006

(22) PCT Filed: Aug. 18, 2011

(86) PCT No.: PCT/US2011/048220
§ 371 (c)(1),
(2), (4) Date: Aug. 14, 2013

(87) PCT Pub. No.: WO2012/027185
PCT Pub. Date: Mar. 1, 2012

(65) Prior Publication Data
US 2014/0081400 A1    Mar. 20, 2014

Related U.S. Application Data

(60) Provisional application No. 61/376,735, filed on Aug. 25, 2010.

(51) Int. Cl.
*G06F 19/00*    (2011.01)
*G06K 9/00*    (2006.01)
(Continued)

(52) U.S. Cl.
CPC ............. *A61F 2/30942* (2013.01); *A61B 19/50* (2013.01); *A61B 2019/502* (2013.01); *A61B 2019/505* (2013.01); *A61B 2019/508* (2013.01); *A61B 2017/00526* (2013.01); *G06T 19/20* (2013.01); *G06T 2210/41* (2013.01); *G06T 2219/2021* (2013.01)

(58) Field of Classification Search
CPC ............. A61B 19/50; A61B 2019/502; A61B 2019/505; A61B 2019/508; A61F 2/30942; G06T 2210/41; G06T 19/20
USPC ............ 700/97–98; 623/16.11; 345/421, 424, 345/442; 382/128
See application file for complete search history.

(56) References Cited

U.S. PATENT DOCUMENTS 6,287,341 B1 * 9/2001 Lee et al. .................. 623/16.11
6,299,649 B1   10/2001 Chang
(Continued)

FOREIGN PATENT DOCUMENTS

WO    WO 0146912 A1    6/2001
WO    WO 2008011268 A2   1/2008
(Continued)

*Primary Examiner* — Ronald Hartman, Jr.

(57) ABSTRACT

A method on a processor customizes a fixation plate for repairing a bone fracture. A digital CAD model of an implant contains smooth analytic geometry representations including NURBS. The CAD geometry is directly manipulated to generate a customized implant CAD model that conforms to the desired region of the bone surface of a patient. Direct manipulation of NURBS geometry is computationally fast and suitable for interactive planning. The patient specific customized implant is produced directly from the generated customized CAD model with a standard CNC machine before surgery. The patient customized implant is implanted in the patient.

20 Claims, 12 Drawing Sheets

(51) Int. Cl.

| | | |
|---|---|---|
| *G06T 15/40* | (2011.01) | |
| *G06T 17/00* | (2006.01) | |
| *G06T 11/20* | (2006.01) | |
| *G06T 19/20* | (2011.01) | |
| *A61F 2/30* | (2006.01) | |
| *A61B 19/00* | (2006.01) | |
| *A61B 17/00* | (2006.01) | |

(56) References Cited

U.S. PATENT DOCUMENTS

| | | | | |
|---|---|---|---|---|
| 6,301,495 | B1 * | 10/2001 | Gueziec et al. | 600/407 |
| 6,701,174 | B1 * | 3/2004 | Krause et al. | 600/407 |
| 7,212,958 | B2 * | 5/2007 | Ascenzi et al. | 703/11 |
| 7,837,621 | B2 * | 11/2010 | Krause et al. | 600/300 |
| 8,126,234 | B1 * | 2/2012 | Edwards et al. | 382/128 |
| 8,160,345 | B2 * | 4/2012 | Pavlovskaia et al. | 382/131 |
| 8,623,026 | B2 * | 1/2014 | Wong et al. | 606/96 |
| 8,644,568 | B1 * | 2/2014 | Hoffmann et al. | 382/128 |
| 8,706,285 | B2 * | 4/2014 | Narainasamy et al. | 700/118 |
| 8,831,302 | B2 * | 9/2014 | Mahfouz | 382/128 |
| 8,855,389 | B1 * | 10/2014 | Hoffmann et al. | 382/128 |
| 2004/0102866 | A1 * | 5/2004 | Harris et al. | 700/117 |
| 2004/0243481 | A1 | 12/2004 | Bradbury | |
| 2007/0226986 | A1 * | 10/2007 | Park et al. | 29/592 |
| 2009/0149977 | A1 * | 6/2009 | Schendel | 700/98 |
| 2011/0087465 | A1 * | 4/2011 | Mahfouz | 703/1 |
| 2011/0144752 | A1 * | 6/2011 | Defelice et al. | 623/16.11 |
| 2012/0010710 | A1 * | 1/2012 | Frigg | 623/16.11 |
| 2012/0010711 | A1 * | 1/2012 | Antonyshyn et al. | 623/16.11 |
| 2012/0194996 | A1 * | 8/2012 | El-Essawy et al. | 361/679.47 |

FOREIGN PATENT DOCUMENTS

| | | |
|---|---|---|
| WO | WO 2008021494 A2 | 2/2008 |
| WO | WO 2009129063 A1 | 10/2009 |

* cited by examiner

200

SEMI-AUTOMATIC CUSTOMIZATION OF PLATES FOR INTERNAL FRACTURE FIXATION

STATEMENT OF RELATED CASES

This case claims priority to and the benefit of U.S. Provisional Patent Application Ser. No. 61/376,735, filed Aug. 25, 2010, which is incorporated herein by reference.

TECHNICAL FIELD

The present invention relates to systems and methods for generating custom orthopedic implants.

BACKGROUND

Standard implants are surgically placed to hold fractured bone segments together. The implants typically have to be deformed to fit a specific patient's bone surface geometry in order to better aid rehabilitation. The traditional approach for implant placement involves inspection of the fracture, aligning bone fragments to their original positions (reduction), physical bending of implants (adaptation) and placement to fit the fractured bone.

This currently has to be performed during the surgical procedure which may prolong the procedure and requires time. Accordingly, new and improved approaches to prepare implants such as fixation plates non-invasively prior to a surgical procedure are required.

SUMMARY OF THE INVENTION

One aspect of the present invention provides methods and systems to create customized implants that conform closely to a patient's bone in order to improve a fit of the implant to a patient's requirement and also, to reduce time spent in OR, to improve precision of a surgical procedure and as a result improves the patient's outcome.

New methods and system for customization of fixation plates for repairing bone fractures are provided as one or more aspects of the present invention.

Digital models of implants are typically available as CAD models that contain smooth analytic geometry representations including Non Uniform Rational B-Spline, from this point forward also identified by its acronym NURBS. In accordance with an aspect of the present invention, a CAD geometry of an implant is directly manipulated by a processor to generate customized implants that conform to the desired region of the bone surface of a patient.

Direct manipulation of NURBS geometry enables an efficient and accurate approach that is also computationally suitable for interactive planning applications.

In accordance with another aspect of the present invention, a patient specific customized implant is produced directly from the generated CAD models with a standard CNC machine or any other computer controlled manufacturing machine before surgery. This approach reduces time spent in OR, improves precision of the procedure and as a result improves the patient's outcome.

In accordance with an aspect of the present invention, a method is provided for creating a customized medical implant, comprising a processor receiving a Computer Aided Design (CAD) model of a medical implant, converting a three dimensional medical image of a bone of patient, to an image of polygonal meshes, computing a guide curve on the image of polygonal meshes of the bone, registering the CAD model to an initial location on the image of the polygonal meshes of the bone, deforming the CAD model in accordance with the guide curve to a customized CAD model and outputting the customized CAD model.

In accordance with another aspect of the present invention a method is provided, wherein the customized CAD model is output to a manufacturing machine that manufactures the customized medical implant.

In accordance with yet another aspect of the present invention a method is provided, further comprising installing the customized medical implant on the bone of the patient.

A corresponding system to perform these methods with a processor is also contemplated and described herein.

DESCRIPTION

Figure 2:
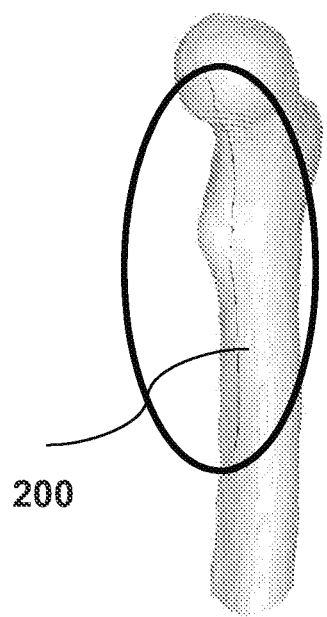
FIG. 2 illustrates a bone patient geometry.
Figure 1:
FIG. 1 illustrates an implant CAD model.
Figure 3:
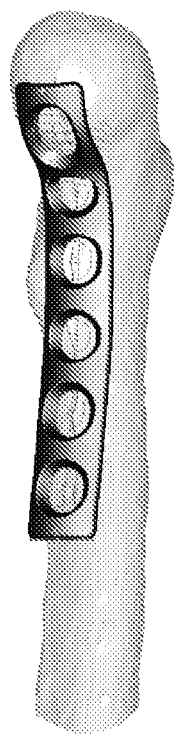
FIG. 3 illustrates an customized implant on a bone.

Aspects of the present invention provide systems and methods for creating custom implants for Open Reduction Internal Fixation (O.R.I.F) type treatments for repairing bone fractures is provided herein as an aspect of the present invention. Standard implants such as the one shown in FIG. 1 are surgically placed to hold fractured bone segments together. The implants typically have to be deformed to fit a specific patient's bone surface geometry in order to better aid rehabilitation. FIG. 1 illustrates a CAD model of standard off-the-shelf implant. FIG. 2 illustrates a polygonal mesh representation of patient bone computed from CT scan or other image of patient. Desired region where implant is to be placed is indicated by ellipse 200. A CAD model customized to conform to desired region of patient's bone surface is illustrated in FIG. 3.

Figure 4:
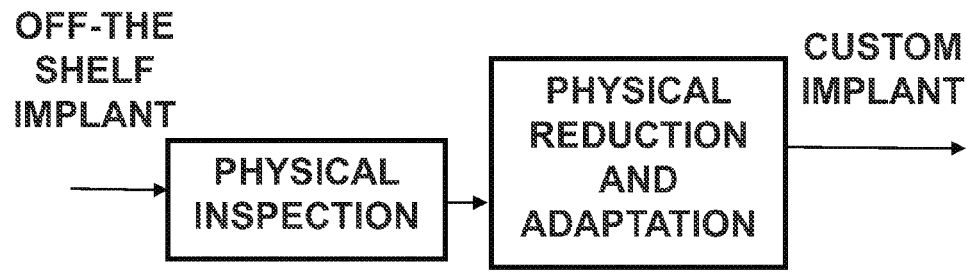
FIG. 4 illustrates an implant adaptation process.

A traditional approach for implant placement involves inspection of the fracture, aligning bone fragments to their original positions (reduction), physical bending of implants (adaptation) and placement to fit the fractured bone and is illustrated in FIG. 4.

With the advent of non-invasive procedures for inspection such as X ray, MRI and CT imaging, there has been a recent impetus on computer assisted preoperative planning and customization of implants to reduce surgeries and operative time as generally described in Fornaro, J. and Keel, M. and Harders, M. and Marincek, B. and Szekely, G. and Frauenfelder, T. An interactive surgical planning tool for acetabular fractures: initial results. Journal of Orthopaedic Surgery and Research 5 (1), 2010, BioMed Central Ltd., Cimerman, M. and Kristan, A., Preoperative planning in pelvic and acetabular surgery: the value of advanced computerised planning modules, Injury 38(4), pp 442-449, 2007, Elsevier and Citak, M. and in Gardner, M. J. and Kendoff, D. and Tarte, S. and Krettek, C. and Nolte, L. P. and Hufner, T. Virtual 3D planning of acetabular fracture reduction. Journal of Orthopaedic Research 26(4), pp 547-552, 2008, John Wiley & Sons.

Figure 5:
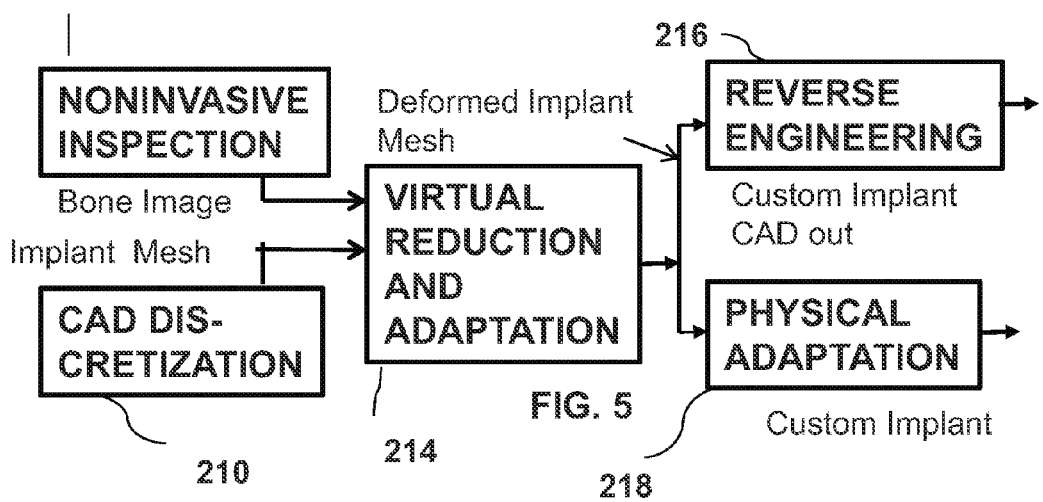
FIG. 5 illustrates a computer assisted non-invasive approach for implant customization.

Noninvasive methods as provided herein utilize information from scanned images of fractured bones to plan reductions and implant adaptations as illustrated in FIG. 5. Digital models of implants are typically available as Computer Aided Design (CAD) models. These can be stored in a library of CAD models and can be selected, as appropriate. CAD models contain smooth analytic representations of the geometry of the models Implant CAD models are commonly first discretized as shown in step 210 to polygonal mesh representations in existing computer aided planning and customization tools as described in Fornaro, J. and Keel, M. and Harders, M. and Marincek, B. and Szekely, G. and Frauenfelder, T. An interactive surgical planning tool for acetabular fractures: initial results. Journal of Orthopaedic Surgery and Research 5 (1), 2010, BioMed Central Ltd. A medical image of the bone is generated in step 212. The implant mesh is modified in accordance with the bone image as shown in step 214. The deformed implant mesh is not enabling for a manufacturing machine and has to be further processed.

Implant models typically contain several fine scale features such as screw threads for assembling implants onto bones. In order to preserve such features during deformation, the meshes typically have to be very fine resulting in very large number of polygons. This in turn burdens the computational algorithms for customization. Accuracy of the planning procedure is dependent on the accuracy of the mesh approximating potentially complicated implant surface. High accuracy typically requires very fine levels of discretization that leads to high computational cost. In addition, in order to manufacture a customized implant, a CAD model of the new deformed geometry is required. The deformed polygonal meshes have to be reverse engineered as shown in step 216 to obtain CAD representations, which may potentially be a very complicated task.

Alternatively, standard implants may be physically adapted based on measurements from adapted meshes as shown in step 218 and described in Formaro, J. and Keel, M. and Harders, M. and Marincek, B. and Szekely, G. and Frauenfelder, T. An interactive surgical planning tool for acetabular fractures: initial results. Journal of Orthopaedic Surgery and Research 5 (1), 2010, BioMed Central Ltd. Such an approach is however a non-trivial and potentially time consuming manual task.

Figure 6:
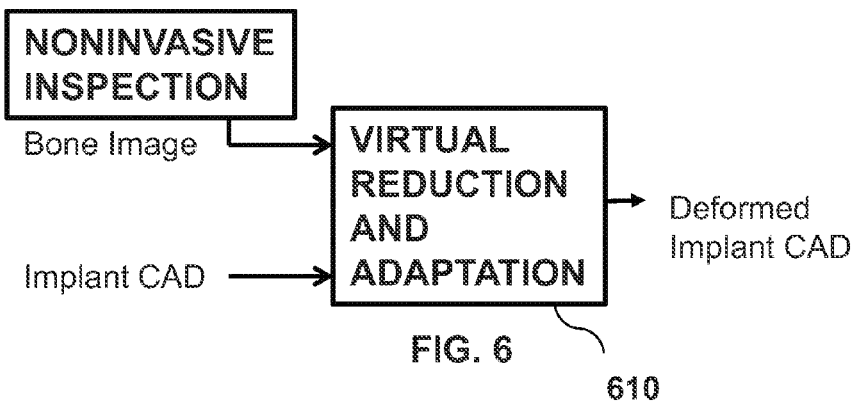
FIG. 6 illustrates a computer assisted non-invasive approach for implant customization in accordance with an aspect of the present invention.

A new method for computer assisted non-invasive implant customization is provided herein as an aspect of the present invention that directly adapts the CAD representation to obtain the customized CAD model and is illustrated in FIG. 6. In fact the new virtual reduction and adaptation step 610 circumvents the previous inefficient processing. The Non Uniform Rational B-Spline (NURBS) geometry representation as described in Cohen, E. and Riesenfeld, R. F. and Elber, G. Geometric modeling with splines: an introduction, 2001, AK Peters Ltd., is used herein on the standard CAD model in order to perform smooth accurate deformation. Non-uniform rational basis spline (NURBS) is a known mathematical model commonly used in computer graphics for generating and representing curves and surfaces which offers great flexibility and precision for handling both analytic and freeform shapes.

NURBS based geometry is manipulated by a set of control points. The deformation procedure is computationally less expensive since much fewer control points are required to manipulate NURBS-based implants; whereas typically, a very large number of polygons are required to manipulate accurate mesh based implant representations. The customized CAD models can then be directly used for manufacturing since NURBS is an industry standard for computer aided design and manufacturing (CAD/CAM).

FIG. 1 illustrates a CAD model of a standard implant that is required to be placed and deformed to fit the indicated region of the bone. FIG. 3 illustrates the customized implant CAD model. As an aspect of the present invention, the adaptation process is guided by a curve on the bone surface. The herein provided aspects of the present invention are quite general and hence extensible to other adaptation techniques. The herein provided examples demonstrate the feasibility and benefits of performing adaption directly with CAD representations.

Axial deformation which is described in Lazarus, F. and Coquillart, S. and Jancene, P. Axial deformations: an intuitive deformation technique. Computer-Aided Design 26 (8), pp 607-613, 1994, Elsevier, is a spatial deformation technique that uses an initial and a deformed axis curve to guide deformation. Lazarus et al. present an interactive deformation technique called Axial Deformations (AxDf). Based on the paradigm of the modeling tool, the axial-deformations technique allows deformations, such as bending, scaling, twisting and stretching, that can be controlled with a 3D axis to be easily specified. Moreover, AxDf can easily be combined with other existing deformation techniques.

This technique is geometry representation independent and can be applied to a set of points defining the geometry. In the case of a mesh, the deforming points are the vertices of the mesh. For a NURBS curve or surface, the deforming points are the control points. Axial deformation is used herein for deforming the control points of all curves and surfaces of a CAD model.

A local frame is defined for every point on the initial axis. Every point to be deformed is mapped on to a point on the axis. Let $S(u)$ be the initial axis. A point $P=(x,y,z)$ to be deformed is mapped to a point on the axis $S(u_p)$. P is then expressed as a point in the local coordinate frame at $S(u_p)$. Let the deformed curve be $D(u)$. The location of the new point $P_d$ in the deformed shape is computed by transforming the local coordinates of P into world coordinates based on the new local frame at $D(u_p)$.

For example, $u_p=z$ when $S(u)$ is linear (i.e., a line segment) and parallel to the Z axis. The local frame at $S(u_p)$ also defines a distance $r_p=\|P-S(u_p)\|$ and an angle $a_p$ that the vector $S(u_p)-P$ makes with the local frame's X axis vector. This gives a parameterization of P $(u_p, r_p, a_p)$ in the local frame at $S(u_p)$. Then $P_d=D(u_p)+r_pV_x$, where $V_x$ is the X axis vector of the frame at $D(u_p)$ rotated by $a_p$ about the Z axis vector of the frame. This technique can be extended to the case where $S(u)$ is non-linear as is described in Lazarus, F. and Coquillart, S. and Jancene, P. Axial deformations: an intuitive deformation technique. Computer-Aided Design 26 (8), pp 607-613, 1994, Elsevier.

Figure 8:
FIG. 8 illustrates an import and initialize implant CAD in accordance with an aspect of the present invention.
Figure 9:
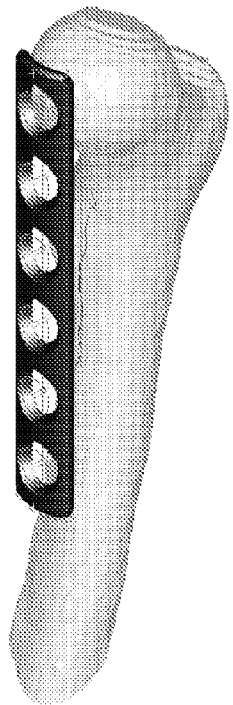
FIG. 9 illustrates a registration of an implant CAD with a bone in accordance with an aspect of the present invention.
Figure 10:
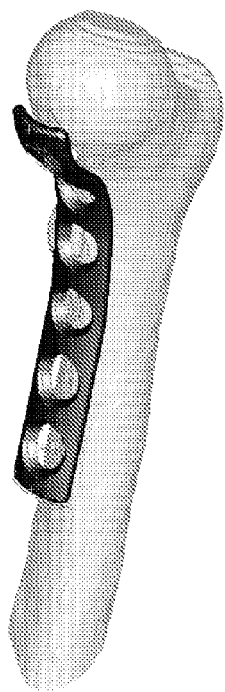
FIG. 10 illustrates an application of a deformation to the implant CAD in accordance with an aspect of the present invention.
Figure 11:
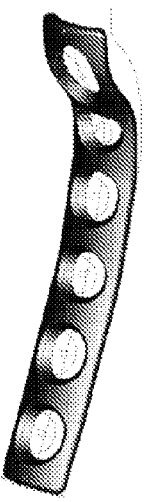
FIG. 11 illustrates an export of the deformed CAD in accordance with an aspect of the present invention.

The fractured bone fragments are converted from scanned images (CT) to polygonal meshes. It is assumed that the reduction procedure has been performed so that bone fragments are placed in their original relative positions. FIGS. 7 to 11 illustrate the steps involved in the aspects of the present approach for creating custom implants. In accordance with one aspect of the present invention the implementation of the approach begins with importing fractured bone fragment meshes. A guide curve 700 is computed on the mesh (-es) and used as the final deformed axis to perform axial deformation (FIG. 7 with guide curve 700 between points 701 and 702). The implant CAD model is imported and prepared for adaptation (FIG. 8). A linear longitudinal axis of the implant is computed for initializing axial deformation. The implant and bone fragments (after reduction) are then registered to an initial location (FIG. 9). The implant CAD model is then deformed based on the guide curve (FIG. 10). The adapted CAD model can then be exported to a standard CAD format and sent for manufacturing (FIG. 11). CAD model processing has been implemented using Open Cascade which is described on-line on Open CASCADE Technology, 3D modeling & numerical simulation. Open Cascade S.A.S. 2010 (URLwww.opencascade.org)

Workflow

Initialize Guide Curve

A user selects a set of points on a path on the mesh fragments that identifies the desired location and placement of the implant. A set of mesh edges connecting the point set is computed and the deformation curve is computed as a B-Spline curve approximation mesh vertices on the connecting path. The curve may have many wiggles depending on the quality of the tessellation of the bone meshes. These wiggles are curve segments with high curvature that cause unnatural and undesirable deformations to the implant when axial deformation is applied. So the curve is first smoothened using a Laplacian technique which is described in Taubin, G. Curve and surface smoothing without shrinkage. Proceedings of Fifth International Conference on Computer Vision, pp 852-857, 1995, which acts as a low pass filter thereby reducing undesirable high curvature features.

Figure 7:
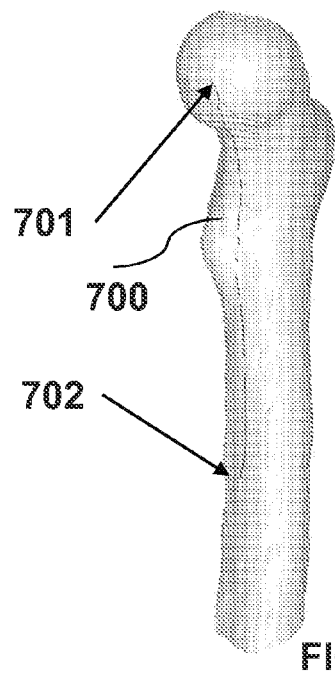
FIG. 7 illustrates an initialization of a guide curve on a bone in accordance with an aspect of the present invention.
Figure 12:
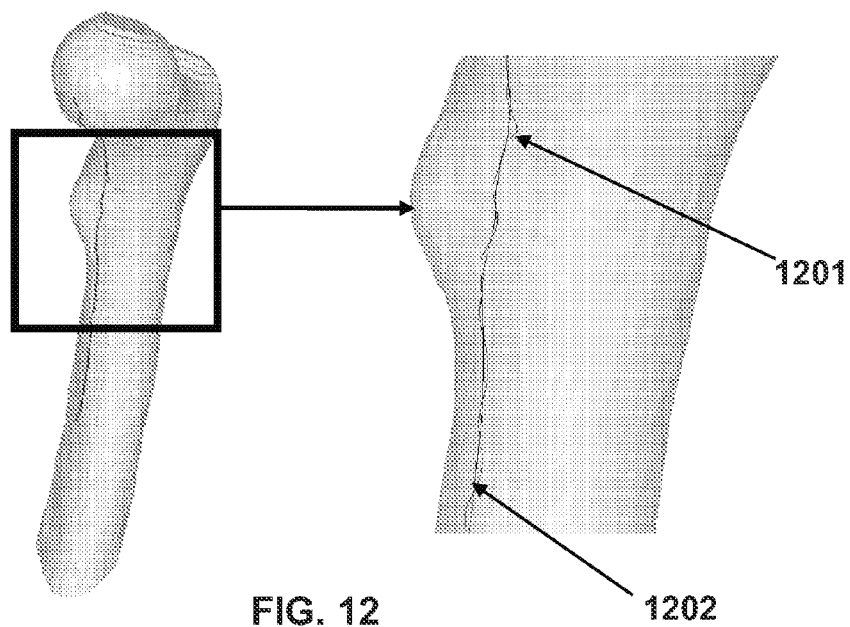
FIG. 12 illustrates smoothing of a guide curve.

In FIG. 7, a single mesh representing the fractured bone is shown for the sake of illustration of the concept. A user selects two points 701 and 702 to define the guide curve path 700. In general, segments of guide curve path may be computed on the independent bone fragments after reduction. The guide curve can still be computed as a B-Spline approximation on the collection of all mesh vertices without any additional processing. FIG. 12 shows a region of the guide curve with a large number of wiggles that smoothened to obtain a better axial deformation curve. The unsmoothed curve in FIG. 12 is shown with wiggles and the smoothened curve has no wiggles. Arrows 1201 and 1202 in FIG. 12 identify wiggles.

Initialize Implant CAD Model

CAD models can contain curve and surface geometry defined by linear (line segments, planes) and quadric (circular arcs, ellipses, cylinders, spheres) analytic representations in addition to the more general NURBS representation. The low degree analytic representations will not be sufficient to represent the deformed geometry of the adapted implant. For example, a deformed cylinder can no longer be represented by the original quadric representation. Deformed geometry is more free form in nature and hence can be well represented by NURBS. Further, all low degree analytic representations used in CAD models can be exactly represented by NURBS as described in Cohen, E. and Riesenfeld, R. F. and Elber, G. Geometric modeling with splines: an introduction. 2001, AK Peters Ltd. and in Farin, G. Curves and surfaces for CAGD: a practical guide, 2002, Morgan Kaufmann Pub. Therefore, first all curves and surfaces in the original CAD model are converted to NURBS using standard techniques as described in Cohen, E. and Riesenfeld, R. F. and Elber, G. Geometric modeling with splines: an introduction, 2001, AK Peters Ltd. and in Farin, G. Curves and surfaces for CAGD: a practical guide, 2002, Morgan Kaufmann Pub.

The NURBS curve and surface representations may not have sufficient degrees of freedom (I.e., control points) to achieve the desired adapted CAD model. In order to obtain smooth deformations especially in highly curved regions, additional degrees of freedom are added. All curves and surface are first degree raised to cubics to ensure smoothness. The number of degrees of freedom to be added is a user-specified factor of the maximum curvature of the deformation guide curve ($d=c_{kmax}$).

Knots are recursively inserted until isoparametric segment lengths between successive knots is lower than d. This ensures that the implant model is flexible so that the deformed model is smooth and geometrically consistent in regions of high curvature deformations. Efficient methods for degree raising and knot insertion are presented in Cohen, E. and Riesenfeld, R. F. and Elber, G. Geometric modeling with splines: an introduction, 2001, AK Peters Ltd.

Register Implant and Bone Fragment(s)

The flexible NURBS model is placed in the desired region using the user selected points on the bone mesh. The current system uses a simplified approach to perform registration. The bottom center of the bounding box of the implant model is placed at the lower end of the guide curve. With the original implant model assumed straight, the bone mesh is rotated to align the first and last point of the guide curve with the model's axis and facing the correct orientation.

Apply Deformation to Interpolated Guide Curve

The flexible NURBS CAD model is deformed using the axial deformation technique discussed above. The model axis is set as the initial curve and the guide curve is set as the final curve. The control points of all the curves and surfaces of the CAD model are transformed using the axial deformation technique. The transformed control points define the geometry of the deformed implant CAD model. Since the final guide curve is smooth, the deformed implant model is also smooth.

The deformed CAD model should not be allowed to intersect the bone mesh geometry. In one embodiment of the current invention, the guide curve is interpolated between the initial axis and the final curve on the bone surface. The implant model is deformed at every step using the interpolated curve and tested for collisions with the bone mesh. If there is a collision, the deformation stops. The user can reset the guide curve and perform the adaptation, if required. In one embodiment of the current invention, the implant CAD model is coarsely tessellated to generate a mesh to perform computationally fast collision detection with the bone mesh.

Interpolation of the guide curve is performed using an arc length parameterization based method that ensures smooth interpolation of curve length as described in Peng, Q. and Jin, X. and Feng, J. Arc-length-based axial deformation and length preserved animation. Computer Animation '97, pp 86-92, 1997.

Figure 13:
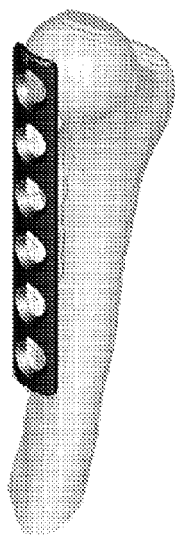
FIGS. 13 to 16 illustrate steps in arc length based interpolation of guide curve for smooth deformation in accordance with an aspect of the present invention.
Figure 14:
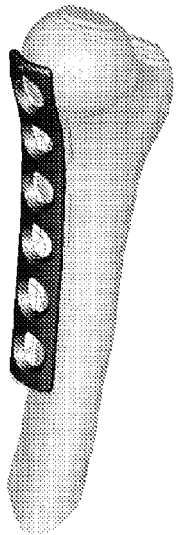
Figure 15:
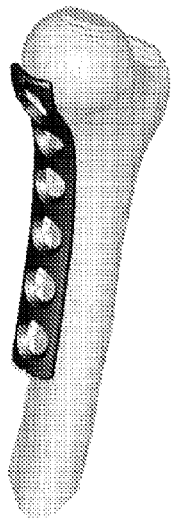
Figure 16:
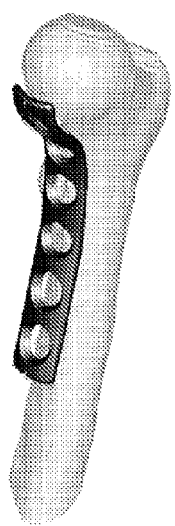

FIGS. 13 to 16 illustrate several steps of the deformation applied to the interpolated guide curves. FIG. 13 illustrates an initial model; FIG. 14 illustrates 33% deformation; FIG. 15 illustrates 67% deformation; and FIG. 16 illustrates a final model.

Export Custom Implant CAD Model

The final adapted implant model is represented as a NURBS based CAD model. This model can then be saved into a standard CAD file format such as IGES or STEP and sent for manufacturing customized implants.

Examples of Other Implant CAD Models

Figure 17:
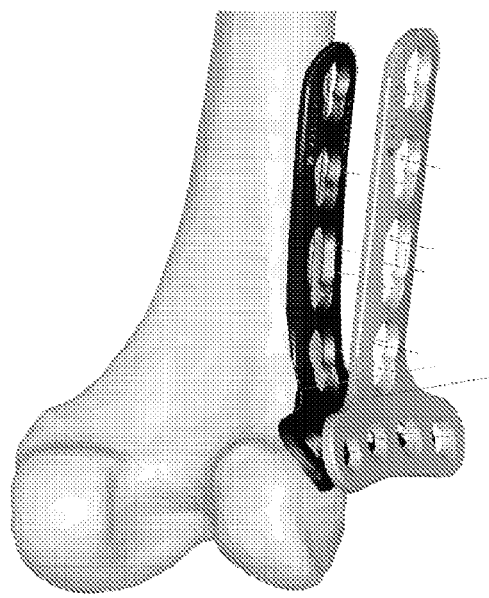
FIGS. 17 to 18 show two views of a customized implant plate on distal femur bone in accordance with an aspect of the present invention.
Figure 18:
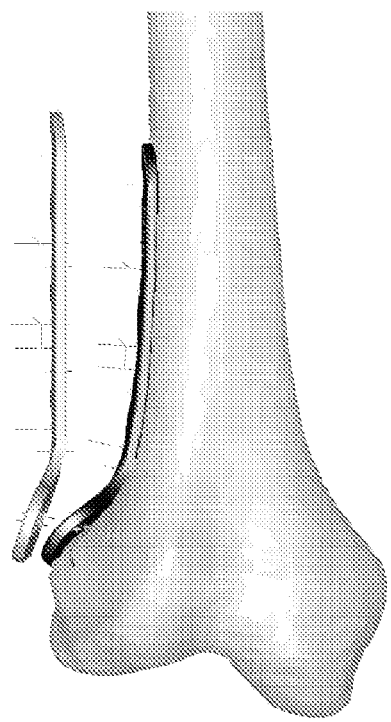

This section presents results on applying the herein provided technique in accordance with one or more aspects of the present invention on two other implant plates on different regions of the femur bone. FIGS. 17 and 18 illustrate an implant plate customized for the distal region of the femur bone. Registered locations (after reduction) of the original implant CAD model are shown in light grey and the adapted models are shown in black. This implant model contains more complicated assembly features such as threaded holes as compared to the implant shown in FIGS. 8 to 11. A mesh representation would require very fine tessellation to retain the high accuracy of the CAD model based proposed approach. The quality of the customized CAD model is comparable with the quality of the original CAD model as illustrated in FIGS. 19 and 20, wherein FIG. 19 illustrates the original implant for a distal femur and FIG. 20 illustrates the customized implant.

Figure 21:
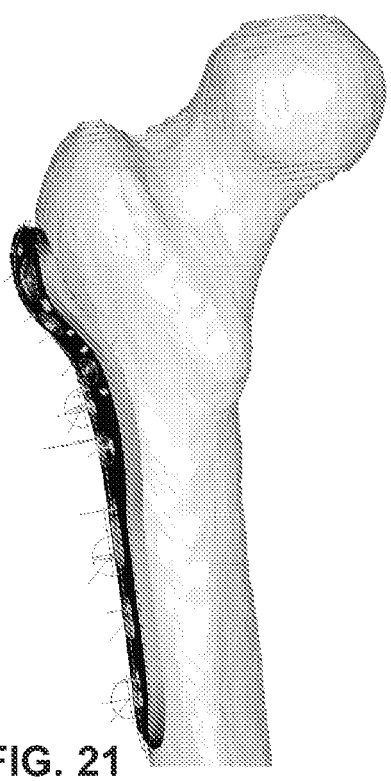
FIGS. 21 to 22 illustrate an image of a human bone that is matched in shape with a modified CAD model of a medical implant in accordance with an aspect of the present invention.
Figure 22:
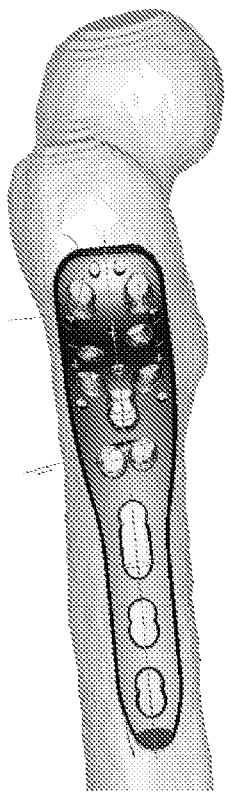
Figure 23:
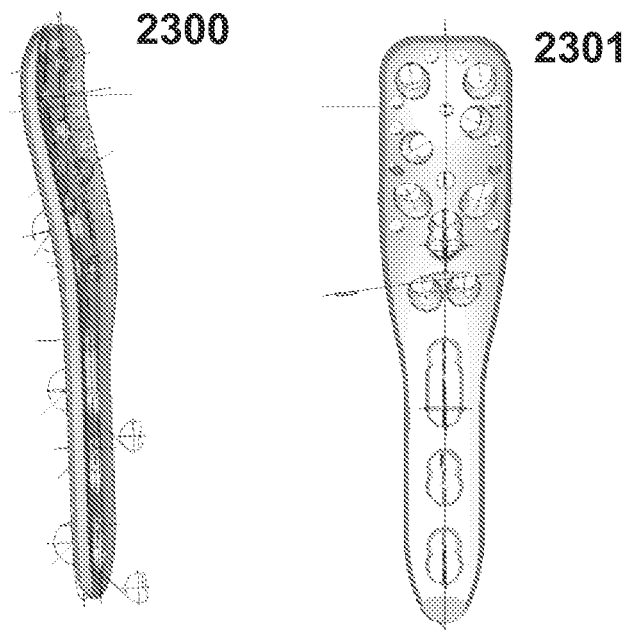
FIG. 23 illustrates different views of a medical implant.
Figure 24:
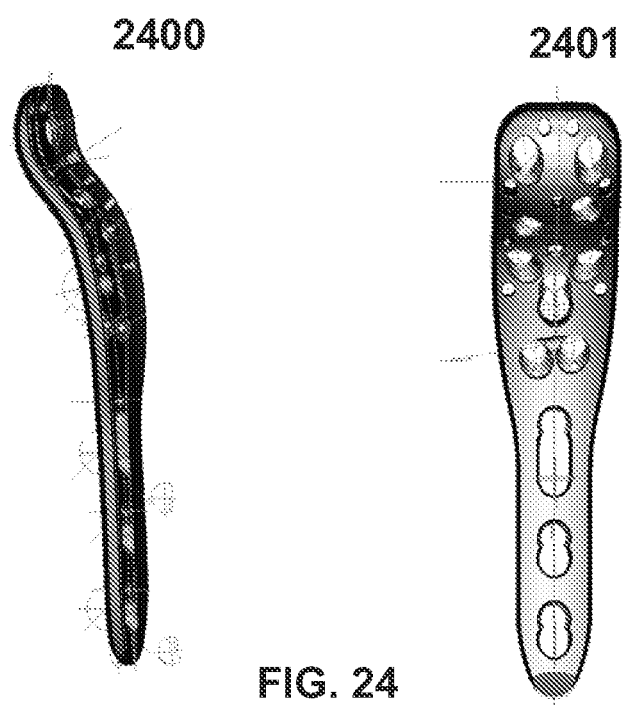
FIG. 24 illustrates different views of implants that are customized for a patient in accordance with an aspect of the present invention.

FIGS. 21 to 24 illustrate the results of applying the herein provided customization technique on an even more complicated model with several assembly features that also include threads. FIGS. 21 and 23 illustrate two views of a customized implant plate on a proximal femur bone. FIGS. 23 and 24 illustrate views 2300 and 2301 of an original implant and views 2400 and 2401 of a customized implant plate. These images illustrate the capability of the herein provided approach in handling very complex implant models.

Figure 19:
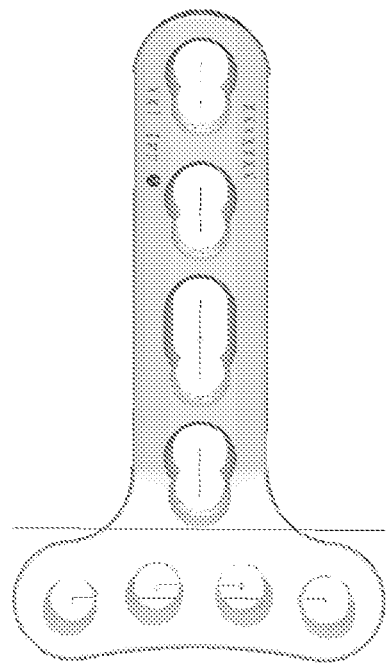
FIG. 19 shows in diagram an original implant for distal femur.
Figure 20:
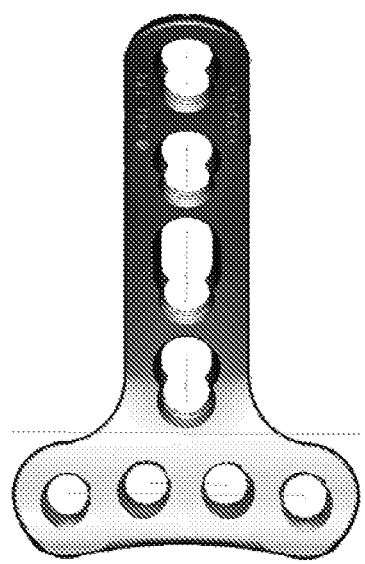
FIG. 20 shows in diagram a customized implant for distal femur in accordance with an aspect of the present invention.

For the implants shown in FIGS. 19 and 20 and in FIGS. 23 and 24, it may be more desirable to approximate an initial curved axis of symmetry instead of using a straight linear axis in order to obtain more intuitive deformations. A curved axis can be determined by computing intersections of the CAD model with several planes along its longitudinal direction and connecting centroids of convex hulls of the sets of planar intersection curves. Open Cascade's BRepAlgoAPI_Section API was tested for computing intersections of planes with CAD models, but this API was not robust and did not compute the results for the given implant models. Therefore, a straight linear axis was used for these models and the results seem reasonably good for the sake of illustrating the herein provided methods in accordance with at least one aspect of the present invention.

A new method for performing fracture implant adaptation to create customized implants has been provided herein as an aspect of the present invention. Digital models of implants are typically available as CAD models that contain smooth analytic geometry representations including NURBS. Existing methods for implant adaptation use tessellated polygonal models obtained by discretization of smooth CAD geometry. Such methods are computationally expensive due to fine tessellation required for higher accuracy, and require reverse engineering to recreate CAD models of customized implants for manufacturing. A herein provided method avoids these issues by directly modifying NURBS geometry to create custom CAD implants that conform to the desired region of the bone surface of patients.

Direct manipulation of NURBS geometry enables an accurate approach that is also computationally suitable for interactive planning applications. Since the flexible CAD model contains an order or magnitude fewer control points than reasonably accurate mesh approximations, the process is computationally less expensive than mesh based methods. Further, the adapted implant is smooth and accurate since NURBS representation is used. The resulting CAD models can then be directly used for manufacturing patient-specific customized implants. Such manufacturing from CAD models is known and include Layered Manufacturing and Computer Numerical Control (CNC) solutions.

The feasibility and benefits of using CAD models directly in interactive preoperative planning tools is described and demonstrated above. Further, it has also been shown herein what the advantages are for using heterogeneous geometry representations in a unified environment where models with smooth geometry (implants, deformation guide curve) as well as discrete geometry (bone mesh, images) can interact with each other and information can be obtained by analyzing all data in a unified environment.

Additional Approaches

The methods as described herein are further improved as follows.

1. Feature preserving deformations: It is desirable to preserve assembly features such as holes and screw threads in the adapted implant model even for large deformations. There are several possible ways to achieve this. Control points can be added only at certain locations in between hole features and only rotation without length or twist type deformations can be allowed. However, such an approach may be difficult to implement for complicated implant models. A better approach is to extract all such features from the CAD model, apply deformation to the body and then reinsert the assembly features to the adapted model. Many CAD systems maintain a feature hierarchy of CAD models and thus will enable implementation of such an approach. This will further enhance the advantages of direct CAD modification instead of mesh based methods.

2. More general deformation: More complicated implant models may require more general spatial deformation techniques defined by a set of guide curves or surfaces.

3. Registration of implant: In one embodiment of the current system, a simplified approach for semiautomatic implant-bone registration has been implemented. This is extended as a further aspect of the present invention by creating more automatic or user assisted registration techniques within an interactive preoperative planning application.

4. Physically based placement: In one embodiment of the current implementation, deformation of the implant is stopped when the implant and bone collide. The guide curve will then have to be reset such that the region of interest on the bone surface is more accessible. This may however not be possible in all situations. A physically based deformation approach, incorporating properties such as elasticity, is applied in a further aspect of the present invention to create better implants for such cases.

Figure 25:
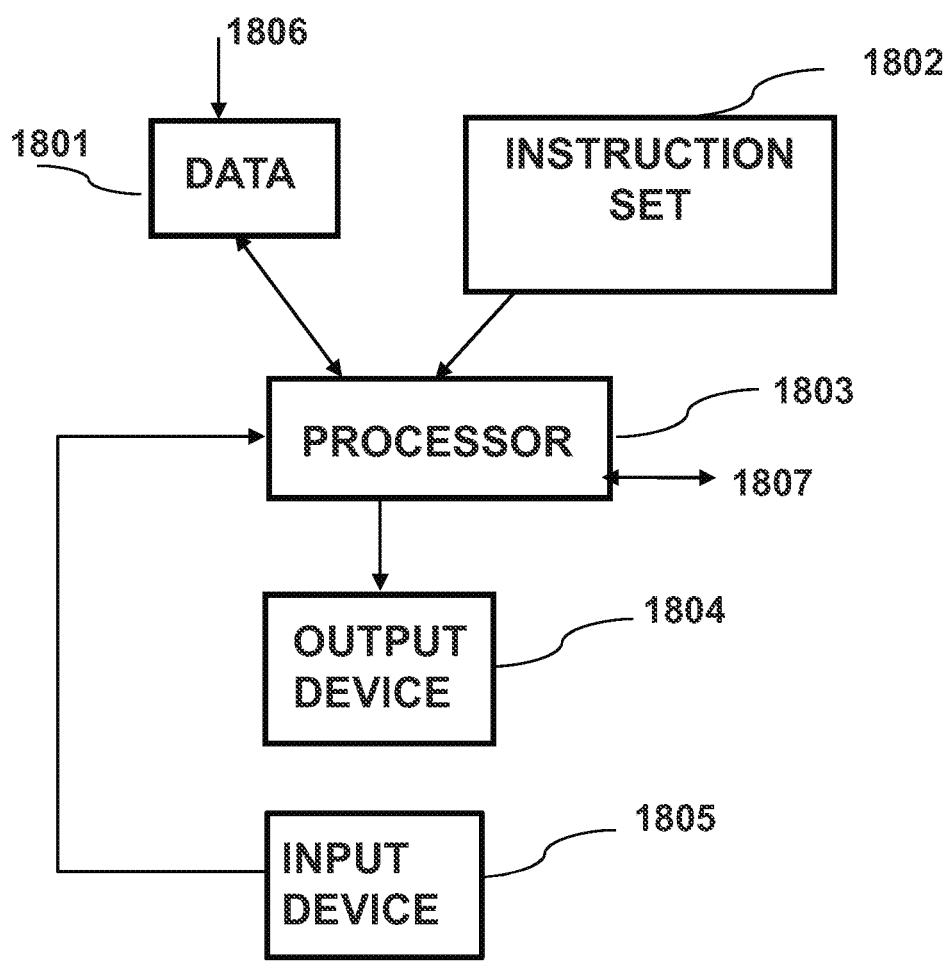
FIG. 25 illustrates a system in accordance with an aspect of the present invention.

A system illustrated in FIG. 25 and as provided herein is enabled for receiving, processing and generating data. The system is provided with data that can be stored on a memory 1801. Data may be obtained from a data source, for instance via an input 1806. Such data may be medical data or any other image data. The data may also be CAD data such as a CAD model of a medical implant. The system has a processor 1803. The processor 1803 is provided or programmed with an instruction set or program executing the methods of the present invention that is stored on a memory 1802 and is provided to the processor 1803, which executes the instructions of 1802 to process the data from 1801. Data, such as image data or deformed CAD data or a CNC file or any other signal resulting from the processor can be outputted on an output device 1804, which may be a display to display data or a data storage device. The output device may also be a storage device that stores the outputted data. Device 1804 may also be a communication device to a manufacturing machine such as a CNC machine.

Device 1804 may also be a display that displays the deformed CAD model in relation to a medical image. The processor also has a communication channel 1807 to receive external data from a communication device and to transmit data to an external device. The system in one embodiment of the present invention has one or more input devices 1805, which may be a keyboard, a mouse or any other device that can generated data to be provided to processor 1803. The processor can be dedicated hardware. However, the processor can also be a CPU or any other computing device that can execute the instructions of 1802. Accordingly, the system as illustrated in FIG. 25 provides a system for data processing resulting from a sensor or any other data source and is enabled to execute the steps of the methods as provided herein as an aspect of the present invention.

Figure 26:
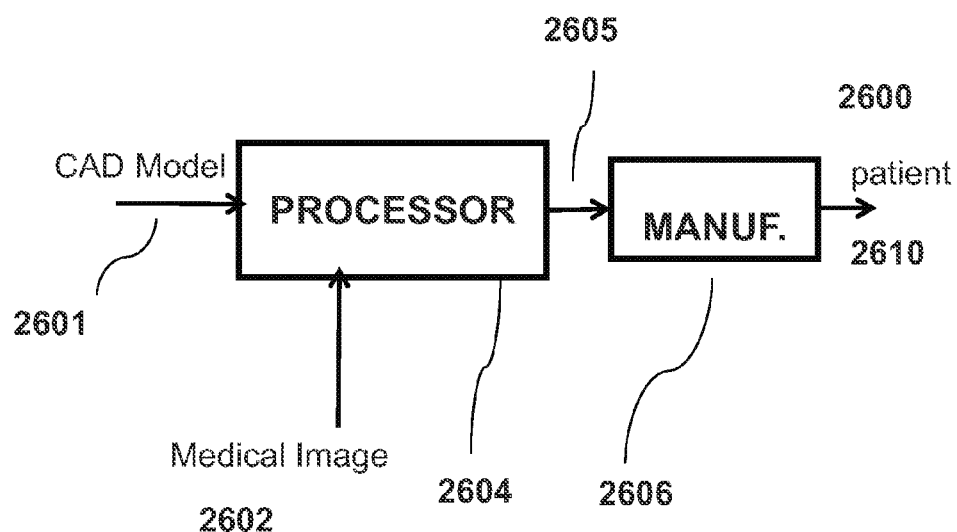
FIGS. 26 to 27 each illustrate a system in accordance with an aspect of the present invention.

The methods as provided herein are, in one embodiment of the present invention, implemented on a system or a computer device. FIG. 26 illustrates a system 2600 used in generating a deformed CAD model in accordance with an aspect of the present invention. A processor 2604 is programmed to perform the steps of a method provided herein in accordance with an aspect of the present invention. On an input 2601 data related to a CAD model of a device, such as a medical implant is received. On an input 2602 data related to a medical image of a patient, such as a patient bone such as a distal femur, is received. The processor 2604 deforms the CAD data to provide a match between the medical implant and the patient's bone and outputs a data file representing the deformed CAD model on 2605. Output 2605 may be connected to a manufacturing system 2606 that is enabled to provide the actual medical implant in its appropriate deformed shape. For instance the deformed CAD model may be provided or transformed into CNC instructions to a CNC machine that mills a material into the deformed medical implant. In a next step the medical implant generated from the deformed CAD model is removed from the manufacturing machine 2606 and implanted in a patient 2610 for instance by a surgeon.

Figure 27:
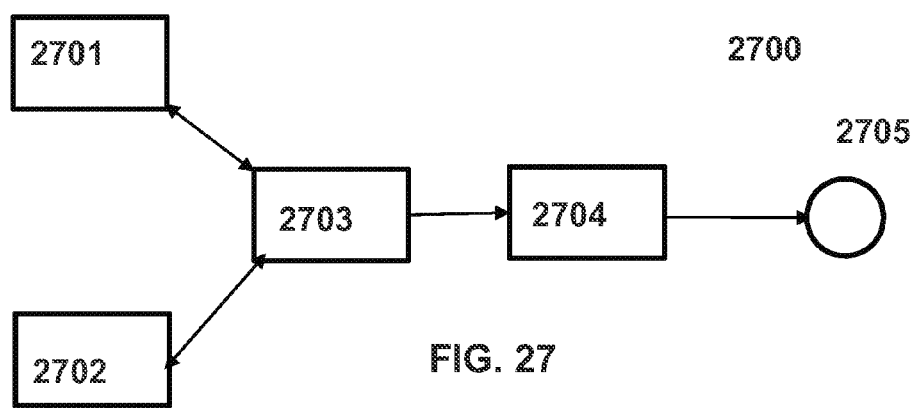

A further embodiment 2700 of the present invention is illustrated in FIG. 27. It contains a system 2703 with a processor to perform the steps of one or more of the methods provided herein. System 2703 provides a patient customized CAD file to a manufacturing system 2704, which may be a CNC system, to manufacture the customized and patient based implant 2705. The system 2703 receives a patient image from a source 2701, which may be a storage device or an imaging device such as a CT scanner. System 2703 also receives a CAD file, for instance in one of the known CAD/CAM formats from a data source 2702. Associated with the CAD file is also implant and manufacturing data that may be attached to the CAD file. In one embodiment of the present invention 2702 is a library, for instance stored on a data storage device that contains CAD data files of at least 2 standard implants. The required standard implant that has to be customized is for instance identified in data included with the image data provided from 2701.

There may be a choice of material for the implant that can be selected or the selected implant will be manufactured in one pre-determined material. In any event, in one embodiment of the present invention data related to a stored CAD model of an implant is provided with manufacturing data related to manufacturing system 2704. For instance, if 2704 includes a CNC machine, then data related to cutting tools, preferred milling speeds and other data related to machining a piece of a pre-determined material is attached to the CAD file, so that the set-up of the manufacturing machine can be done based on data that is part of the customized CAD file. In a further embodiment of the present invention, an order of milling steps by manufacturing machine 2704 may be done based on an analysis of the customized CAD file by system 2704. In a further embodiment an order of at least two milling or cutting steps may be pre-set in the standard CAD file, including a switching of tools. Availability of such data will minimize the need for pre-manufacturing planning and human intervention during manufacturing.

In one embodiment of the present invention the storage or image device 2701 and the library 2702, the system 2703 and the manufacturing system are 2704 are all connected via a network. In a further embodiment the network is the Internet. In yet a further embodiment of the present invention the system 2703 is authorized to receive data from 2701 and 2702 and 2704 is authorized to receive data from 2703.

Figure 28:
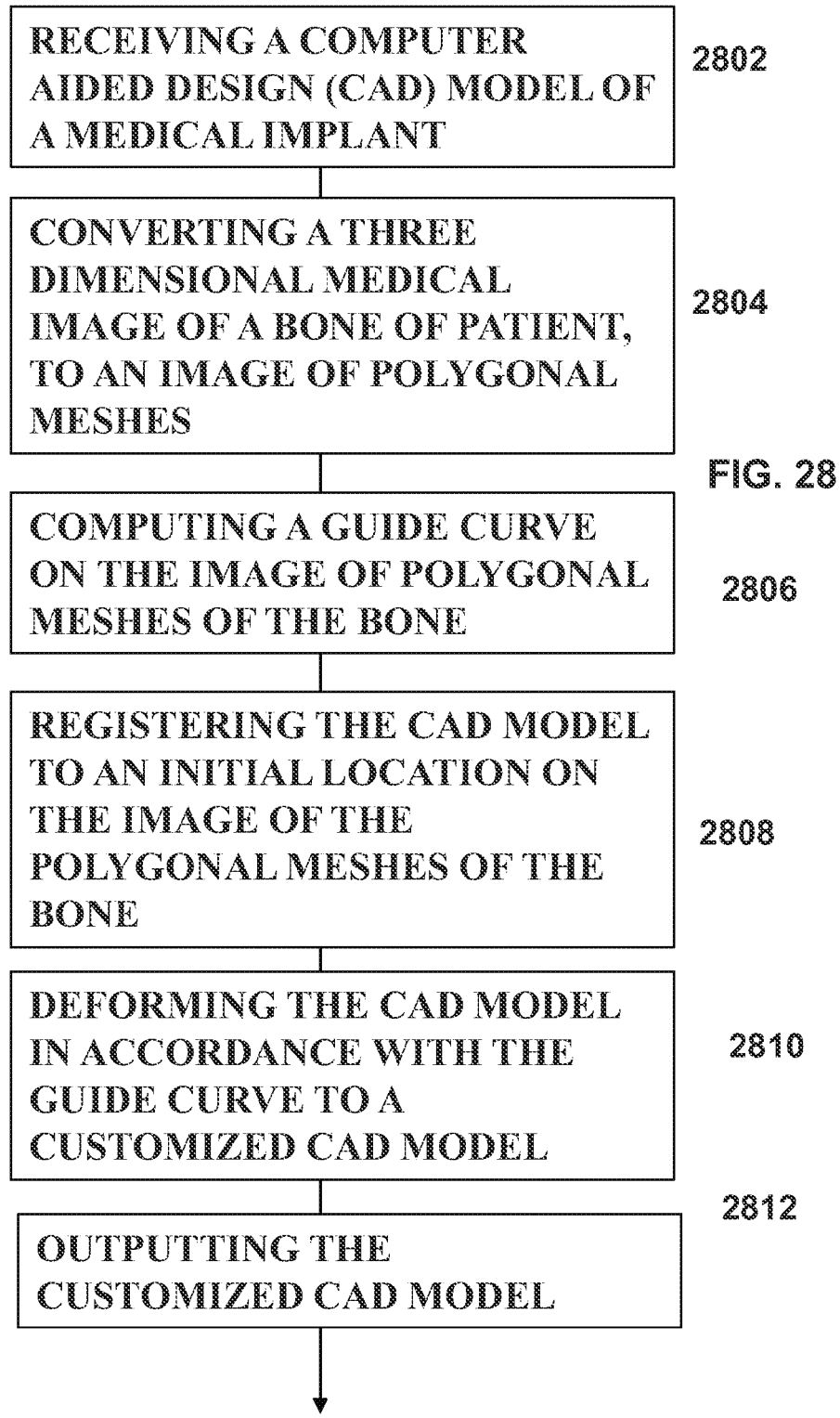
FIG. 28 illustrates steps in accordance with an aspect of the present invention.

In summary, and in accordance with an aspect of the present invention and as illustrated in FIG. 28, a method is provided for creating a customized medical implant, comprising a processor: receiving a Computer Aided Design (CAD) model of a medical implant (2802), converting a three dimensional medical image of a bone of patient to an image of polygonal meshes (2804), computing a guide curve on the image of polygonal meshes of the bone (2806), registering the CAD model to an initial location on the image of the polygonal meshes of the bone (2808), deforming the CAD model in accordance with the guide curve to a customized CAD model (2810) and outputting the customized CAD model (2812).

The customized CAD model can then be output to a manufacturing machine that manufactures the customized medical implant. The customized medical implant can be installed on the bone of the patient. The manufacturing machine can be a Computer Numerical Controlled (CNC) machine.

Also in summary, a set of points on a path in the image of polygonal meshes of the bone that defines the guide curve is selected and a deformation curve is computed as a B-Spline curve approximation of mesh vertices on a connecting path. A processor processes the deformation curve to remove a wiggle. The processor converts all curves and surfaces in the CAD model to Non Uniform Rational B-Spline (NURBS) representations in the CAD model. The processor interpolates in a plurality of steps an interpolated deformation curve located between an axis defined by the initial location and the guide curve. Testing is performed for a collision between the interpolated deformation curve and the image of the polygonal meshes of the bone. A degree of freedom that is associated with a maximum curvature of the guide curve can be increased.

Further in summary, the CAD model is selected from a library containing a plurality of predetermined CAD models.

In accordance with another aspect of the present invention involves a method of for creating a customized medical implant, comprising a processor: receiving a Computer Aided Design (CAD) model of a medical implant; converting a three dimensional medical image of a bone of patient, to an image of polygonal meshes; computing a guide curve on the image of polygonal meshes of the bone; registering the CAD model to an initial location on the image of the polygonal meshes of the bone; deforming the CAD model in accordance with the guide curve to a customized CAD model; and outputting the customized CAD model.

Further, in summary, a computer system is provided, wherein the processor: selects a set of points on a path in the image of polygonal meshes of the bone that defines the guide curve, computes a set of mesh edges connecting the set of points, and computes a deformation curve as a B-Spline curve approximation of mesh vertices on a connecting path.

In one embodiment of the present invention a CAM or any other manufacturing machine receives the customized CAD file and manufactures a customized implant. After removal from the machine the customized implant may receive further processing and it may undergo additional treatment, including finalizing treatment such as annealing, hardening, polishing, sterilizing, testing, marking or any other treatment that is required to prepare for surgical insertion. The custom implant is then provided to a surgeon or a surgical robot in an operating room and is implanted in the patient. The patient receives and will use the customized implant.

The following references provide background information generally related to the present invention and are hereby incorporated by reference: Lazarus, F. and Coquillart, S. and Jancene, P. Axial deformations: an intuitive deformation technique. Computer-Aided Design 26 (8), pp 607-613, 1994, Elsevier. Fornaro, J. and Keel, M. and Harders, M. and Marincek, B. and Szekely, G. and Frauenfelder, T. An interactive surgical planning tool for acetabular fractures: initial results. Journal of Orthopaedic Surgery and Research 5 (1), 2010, BioMed Central Ltd., Taubin, G. Curve and surface smoothing without shrinkage. Proceedings of Fifth International Conference on Computer Vision, pp 852-857, 1995, Cohen, E. and Riesenfeld, R. F. and Elber, G. Geometric modeling with splines: an introduction. 2001, AK Peters Ltd., Peng, Q. and Jin, X. and Feng, J. Arc-length-based axial deformation and length preserved animation. Computer Animation '97, pp 86-92, 1997, Open CASCADE Technology, 3D modeling & numerical simulation. Open Cascade S.A.S. 2010 (URL www.opencascade.org), Farin, G. Curves and surfaces for CAGD: a practical guide, 2002, Morgan Kaufmann Pub., Cimerman, M. and Kristan, A. Preoperative planning in pelvic and acetabular surgery: the value of advanced computerised planning modules. Injury 38(4), pp 442-449, 2007, Elsevier, Citak, M. and Gardner, M. J. and Kendoff, D. and Tarte, S. and Krettek, C. and Nolte, L. P. and Hufner, T. Virtual 3D planning of acetabular fracture reduction. Journal of Orthopaedic Research 26(4), pp 547-552, 2008, John Wiley & Sons.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims.

The invention claimed is:

1. A method for creating a customized medical implant, comprising a processor:
    receiving a Computer Aided Design (CAD) model of a medical implant;
    converting a three dimensional medical image of a bone of patient, to an image of polygonal meshes;
    computing a guide curve on the image of polygonal meshes of the bone;
    registering the CAD model to an initial location on the image of the polygonal meshes of the bone;
    deforming the CAD model in accordance with the guide curve to a customized CAD model; and
    outputting the customized CAD model.

2. The method of claim 1, wherein the customized CAD model is output to a manufacturing machine that manufactures the customized medical implant.

3. The method of claim 2, further comprising installing the customized medical implant on the bone of the patient.

4. The method of claim 1, further comprising:
    interactively selecting a set of points on a path in the image of polygonal meshes of the bone that defines the guide curve.

5. The method of claim 4, wherein a set of mesh edges connecting the set of points is computed by the processor and a deformation curve is computed as a B-Spline curve approximation of mesh vertices on a connecting path.

6. The method of claim 5, wherein the processor processes the deformation curve to remove a wiggle.

7. The method of claim 1, further comprising the processor converting all curves and surfaces in the CAD model to Non Uniform Rational B-Spline (NURBS) representations in the CAD model.

8. The method of claim 1, further comprising the processor interpolating in a plurality of steps an interpolated deformation curve located between an axis defined by the initial location and the guide curve.

9. The method of claim 8, further comprising testing for a collision between the interpolated deformation curve and the image of the polygonal meshes of the bone.

10. The method of claim 1, further comprising increasing a degree of freedom that is associated with a maximum curvature of the guide curve.

11. The method of claim 1, wherein the CAD model is selected from a library containing a plurality of predetermined CAD models.

12. A system to create a customized implant, comprising:
    a memory enabled to store and retrieve data, including instructions;
    a processor enabled to execute instructions to perform the steps:
        receiving a Computer Aided Design (CAD) model of an implant;
        converting a three dimensional medical image of a bone of patient to an image of polygonal meshes;
        computing a guide curve on the image of polygonal meshes of the bone;
        registering the CAD model to an initial location on the image of the polygonal meshes of the bone;
        deforming the CAD model in accordance with the guide curve to a customized CAD model; and
        outputting the customized CAD model on an output.

13. The system of claim 12, further comprising a manufacturing machine that receives the customized CAD model and manufactures the customized implant based on the customized CAD model.

14. The system of claim 13, wherein the manufacturing machine is a Computer Numerical Controlled (CNC) machine.

15. The system of claim 12, wherein the processor:
selects a set of points on a path in the image of polygonal meshes of the bone that defines the guide curve;
computes a set of mesh edges connecting the set of points; and
computes a deformation curve as a B-Spline curve approximation of mesh vertices on a connecting path.

16. The system of claim 12, wherein the processor:
converts all curves and surfaces in the CAD model to Non Uniform Rational B-Spline (NURBS) representations in the CAD model.

17. The system of claim 12, wherein the processor:
interpolates a plurality of interpolated deformation curves located between an axis defined by the initial location and the guide curve.

18. The system of claim 12, wherein the processor:
increases a degree of freedom that is associated with a maximum curvature of the guide curve.

19. The system of claim 12, wherein the CAD model is provided from a storage device containing a library of at least two CAD models for medical implants.

20. The system of claim 12, comprising a library of predetermined CAD models from which the CAD model of the implant is selected.

* * * * *